(12) United States Patent
Kupferschmid

(10) Patent No.: US 11,015,642 B2
(45) Date of Patent: May 25, 2021

(54) BENT TUBULAR SHAFT AND METHOD FOR PRODUCING THE SAME

(71) Applicant: Aesculap AG, Tuttlingen (DE)

(72) Inventor: Bernhard Kupferschmid, Emmingen-Liptingen (DE)

(73) Assignee: AESCULAP AG, Tuttlingen (DE)

( * ) Notice: Subject to any disclaimer, the term of this patent is extended or adjusted under 35 U.S.C. 154(b) by 27 days.

(21) Appl. No.: 16/589,376

(22) Filed: Oct. 1, 2019

(65) Prior Publication Data
US 2020/0032835 A1 Jan. 30, 2020

Related U.S. Application Data

(62) Division of application No. 14/275,498, filed on May 12, 2014, now Pat. No. 10,473,144.

(30) Foreign Application Priority Data

May 13, 2013 (DE) .......................... 102013208729.2

(51) Int. Cl.
*F16C 1/20* (2006.01)
*A61B 17/29* (2006.01)
(Continued)

(52) U.S. Cl.
CPC .............. *F16C 1/205* (2013.01); *A61B 17/29* (2013.01); *B21K 1/06* (2013.01);
(Continued)

(58) Field of Classification Search
CPC .... A61B 2017/2901; A61B 2017/2902; A61B 2017/2904; A61B 2017/2905;
(Continued)

(56) References Cited

U.S. PATENT DOCUMENTS

| 2,171,907 A | 9/1939 | Beehler et al. |
| 3,685,335 A | 8/1972 | Kowal |
| (Continued) | | |

FOREIGN PATENT DOCUMENTS

| DE | 19520717 A1 | 12/1996 |
| DE | 69319199 T2 | 10/1998 |
| (Continued) | | |

OTHER PUBLICATIONS

Entire patent prosecution history of U.S. Appl. No. 14/275,498, filed May 12, 2014, entitled, "Bent Tubular Shaft and Method for Producing the Same."

*Primary Examiner* — Christopher M Koehler

(57) ABSTRACT

A tubular shaft for a tubular shaft instrument includes a hollow shaft component, an actuating rod arranged in the hollow shaft component, and functional elements that are attached at the distal ends of the shaft component and/or of the actuating rod. The actuating rod is axially displaceable relative to the hollow shaft component to move the distal sections of the functional elements toward one another, past one another, and/or away from one another. The actuating rod includes at least one bending area in which flexible segments and support segments alternate and in which the actuating rod has significantly less bending resistance than outside the at least one bending area. A friction-reducing layer on the at least one bending area of the actuating rod reduces the friction of the actuating rod on the inside wall of the shaft component.

8 Claims, 2 Drawing Sheets

(51) Int. Cl.
   *B21K 1/06* (2006.01)
   *A61B 17/00* (2006.01)
   *F16C 1/00* (2006.01)
(52) U.S. Cl.
   CPC ............... *A61B 2017/00526* (2013.01); *A61B 2017/00845* (2013.01); *A61B 2017/00946* (2013.01); *A61B 2017/2902* (2013.01); *A61B 2017/2904* (2013.01); *A61B 2017/2931* (2013.01); *F16C 1/00* (2013.01); *F16C 2316/10* (2013.01); *Y10T 29/49908* (2015.01); *Y10T 74/20456* (2015.01)
(58) Field of Classification Search
   CPC ...... A61B 2017/2908; F16C 1/10; F16C 1/20; F16C 1/205; F16C 1/00; Y10T 29/49908; B21D 7/00; B21D 7/0222; B21D 7/10; B21K 1/063
   See application file for complete search history.

(56) References Cited

U.S. PATENT DOCUMENTS

| | | | |
|---|---|---|---|
| 4,292,834 A | 10/1981 | Tishler et al. | |
| 5,286,253 A | 2/1994 | Fucci | |
| 5,615,572 A | 4/1997 | Johnson et al. | |
| 5,833,692 A * | 11/1998 | Cesarini | A61B 17/32002 606/79 |
| 5,922,003 A | 7/1999 | Anctil et al. | |
| 6,883,360 B2 | 4/2005 | Bates et al. | |
| 7,743,636 B2 | 6/2010 | Rusch | |
| 2003/0028207 A1 | 2/2003 | Lang et al. | |
| 2005/0177168 A1 | 8/2005 | Brunnett et al. | |
| 2008/0071303 A1 | 3/2008 | Hacker et al. | |
| 2010/0024515 A1 | 2/2010 | Hough | |
| 2010/0234687 A1 * | 9/2010 | Azarbarzin | A61B 17/00234 600/201 |
| 2010/0268254 A1 * | 10/2010 | Golden | A61B 17/1285 606/142 |
| 2011/0079627 A1 | 4/2011 | Cardinale et al. | |
| 2011/0230867 A1 | 9/2011 | Hirschfeld et al. | |
| 2011/0245812 A1 | 10/2011 | Blocher et al. | |
| 2011/0276083 A1 | 11/2011 | Shelton et al. | |
| 2014/0114293 A1 | 4/2014 | Jeong et al. | |

FOREIGN PATENT DOCUMENTS

| | | |
|---|---|---|
| DE | 102010011926 A1 | 9/2011 |
| EP | 0577423 A2 | 1/1994 |

* cited by examiner

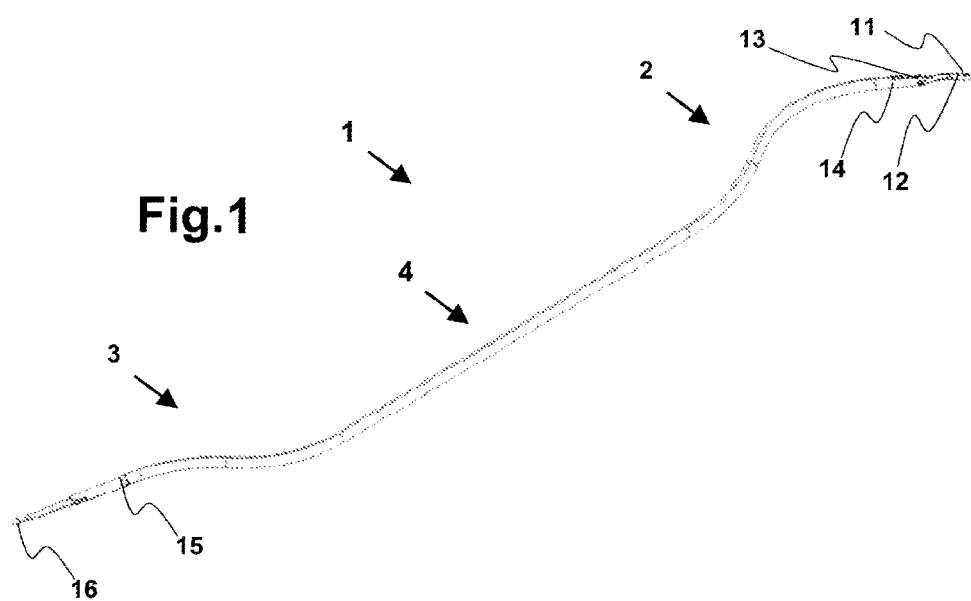
Fig.1
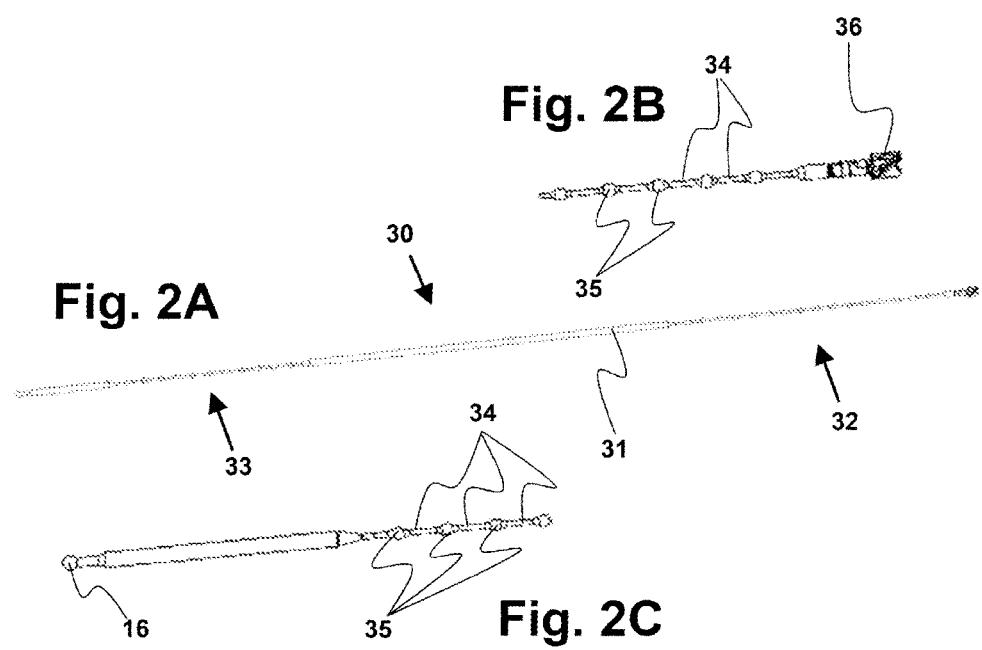
Fig. 2A
Fig. 2B
Fig. 2C

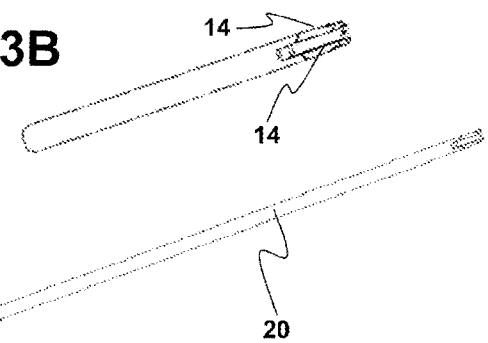
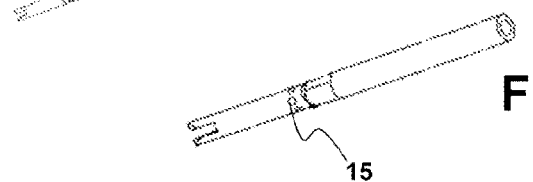
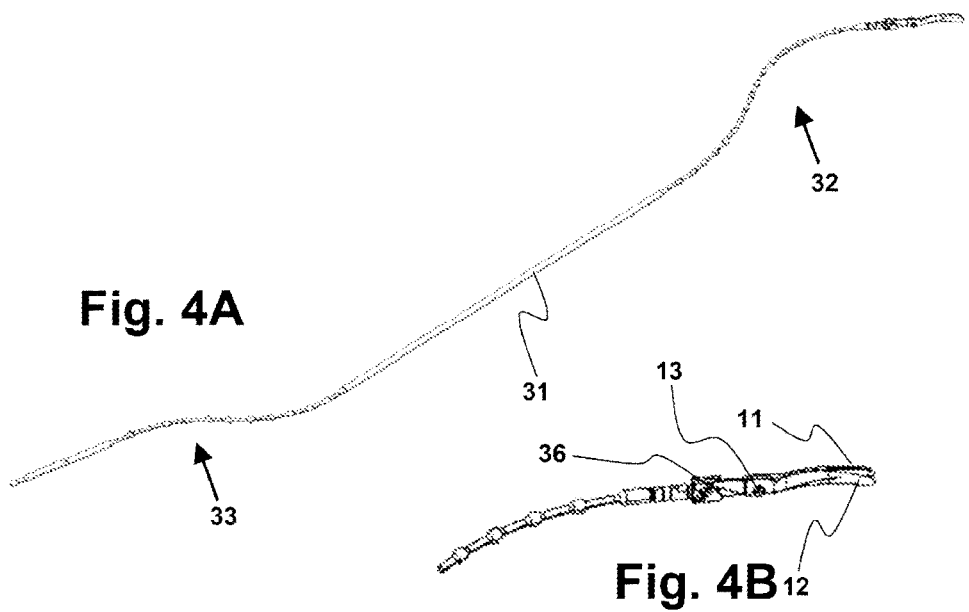

BENT TUBULAR SHAFT AND METHOD FOR PRODUCING THE SAME

CROSS-REFERENCE TO RELATED APPLICATIONS

This application is related to and claims the benefit of priority under 35 U.S.C. § 120 of U.S. application Ser. No. 14/275,498, filed May 12, 2014, which claims the benefit of priority under 35 U.S.C. § 119 of German Application No. 10 2013 208 729.2, filed May 13, 2013. The contents of U.S. application Ser. No. 14/275,498 and of German Application No. 10 2013 208 729.2 are incorporated by reference herein in their entireties.

FIELD

The disclosed embodiments relate to a bent tubular shaft or a tubular shaft instrument as well as a process for producing the same as well as a tubular shaft instrument with a bent tubular shaft of this type.

BACKGROUND

Numerous tubular shaft instruments and thus also numerous tubular shafts are known from the related art. For example, European patent application EP 0577 423 A2 discloses a classic tubular shaft instrument in which a push and pull rod can be moved back and forth axially in its own shaft to allow the jaw part of the tubular shaft instrument to open and close. In this process, the back-and-forth movement of the push and pull rod is transmitted to the halves of the jaw part via a joint mechanism. The push and pull rod can be constructed as a rigid rod. This principle does not facilitate the production of bent tubular shafts.

Tubular shaft instruments with bent tubular shaft are also already known from the related art. For example, German patent application DE 195 20 717 A1 discloses a tubular shaft instrument having a bent tubular shaft. This tubular shaft instrument employs a shaft having a straight proximal area and bent distal area. In the straight proximal area a rigid rod is used as push and pull rod, to the distal end of which a flexible push and pull rod is attached. The flexible push and pull rod is comprised of a rod in which a plurality of circumferential groves is incorporated, which reduces the cross-section of the rod such that the originally essentially rigid rod becomes flexible. Segments are left between the grooves where the push and pull rod retains its original diameter. These segments enable the push and pull rod to be correctly guided and supported in the bent section of the shaft. The push and pull rod tends in the bent shaft segment to assume not the intended shape of an arc, as it is prescribed by the bent area of the shaft, but rather the shape of a polygonal curve. In this context the number and spacing of support segments determines the shape of the polygonal curve. However, a tubular shaft constructed in this manner can be provided only with a single bend area.

If multiple bent areas are supposed to be provided on a tubular shaft instrument that are to be connected, for example, by straight sections, the entire push and pressure rod must be formed with grooves and support segments, because such type of tubular shaft cannot otherwise be assembled. The straight rigid sections then cannot be pushed through the bends in the shaft. However, if a push and pull rod that is equipped with grooves and support segments over the entire length is used, the inner friction of the tubular shaft is increased greatly. This is because a push rod soft enough to bend tends to deviate laterally and to press against the shaft from inside, which leads to additional friction. With a straight rigid rod, this virtually never happens. Additionally, with a push and pull rod that is flexible throughout its entire length, the play between the actuation unit on the proximal end of the tubular shaft and the functional unit on the distal end of the tubular shaft increases, which compromises the operation of the instrument.

SUMMARY

One aspect of the disclosed subject matter provides a tubular shaft which can have a plurality of bent sections without causing excessive inner friction in the tubular shaft. A further aspect of the disclosed subject matter seeks to provide a bent tubular shaft having minimal play. Yet another aspect of the disclosed subject matter seeks to provide a process for producing such a tubular shaft as well as a tubular shaft instrument with a bent tubular shaft of the type specified.

It is advantageous to place the functional elements at the actuating rod and the shaft component before the tubular shaft is bent, because the actuating rod and the shaft component then no longer have to be secured separately from moving against one another for the bending, since this can be handled by the functional elements.

With a tubular shaft having this construction, it is possible to assemble the tubular shaft in linear and/or unbent form and to subsequently bend it into the desired shape. Furthermore, the assembly of the actuating rod and the shaft component is greatly simplified as compared to a tubular shaft with which the components are assembled in the already bent shape. The term "bent components" within the scope of this application not only refers to components that have been bent from some sort of starting shape into a different shape but also components that have been produced in a shape that has at least one area that follows the shape of a bend.

BRIEF DESCRIPTION OF THE DRAWING FIGURES

FIG. 1 shows an isometric view of a tubular shaft according to an exemplary embodiment;

FIGS. 2A-2C show isometric views of an actuating rod of a tubular shaft according to the exemplary embodiment in FIG. 1 in the unbent condition;

FIGS. 3A-3C show isometric views of a shaft sleeve of a tubular shaft according to the exemplary embodiment in FIG. 1 in the unbent condition; and FIGS. 4A and 4B show isometric views of an actuating rod of a tubular shaft according to the exemplary embodiment in FIG. 1 in the bent condition.

DETAILED DESCRIPTION

An exemplary embodiment of the disclosed subject matter is described in detail in the following with reference being made to the figures.

The actuating rod 30, i.e. the bending areas 32, 33 of the same, is/are milled from a cylindrical rod and are therefore formed as a single piece. In the straight area 31, the actuating rod 30 is essentially to be considered rigid with respect to the forces occurring during the bending process and proper use. At the distal end of the actuating rod 30, a sliding component 36 is provided having two guide tracks with a cam protruding into each that is provided on the proximal end of each functional elements 11, 12 and inserts into the slide element. Advantageously, the sliding component 36 is axially rotatable in relation to the actuating rod 30 not only in this exemplary embodiment, which means that during insertion of the actuating rod 30 into the shaft sleeve 20, attention does not have to be paid to the alignment of the actuating rod 30.

For the assembly of the tubular shaft 1 according to this exemplary embodiment, two pieces of shrink tubing (not shown) are pushed over the two bending areas 32, 33 of the actuating rod 30 and shrunk through heating. The proximal end of the actuating rod 30 is then inserted into the opening on the distal end of the shaft sleeve 20 and pushed into the shaft sleeve 20 until only the sliding element 36 is protruding at the front (distally) from the shaft sleeve 20. The cams of the functional parts 11, 12 are then threaded into the guide tracks, and the actuating rod 30 is then pushed a bit further into the shaft sleeve 20 until the bearing holes of the functional parts align with the bearing holes in the bars 14 of the shaft component. A bearing axle is then pushed through the bearing holes of the bars 14 and the functional parts 11, 12 and affixed to the bars 14.

Finally, the tubular shaft 1 assembled in this manner is bent at the points at which the bending areas 32, 33 of the actuating rod 30 are arranged on the interior of the shaft sleeve 20 and the tubular shaft 1 is placed into the desired shape in this manner.

According to further exemplary embodiments of the disclosed subject matter, the friction-reducing layer may also consist of or include a coating, put-on half shells or partial shells and/or an injection molded material. The friction-reducing layer may either be provided only at the bending areas 32, 33 or over the entire length of the actuating rod 30. It is also possible for the friction-reducing layer to be provided at the bending areas 32, 33 only at the spacers, since the flexible segments do not come into contact with the shaft sleeve and compensation of the deformations at the flexible segments is not required.

The bending areas may also be formed in a different manner. The uniform string-of-pearls shape previously shown can be modified to the extent that the support segments have different spacing with respect to one another, that the flexible segments have different cross-sectional areas and/or shapes and/or are arranged outside the longitudinal direction of the actuating rod.

If more than one bending area is provided in an exemplary embodiment, the bends in each bending area may lie in one and the same plane. As an alternative to this, the planes in which the bending in the individual bending areas takes place may be skewed with respect to one another. As another alternative, it is also possible for a bending area to be simultaneously bent in multiple spatial directions such that the tubular shaft, for example, takes on a spiral shape in this section.

A person skilled in the art may furthermore combine the described features of the tubular shaft in any suitable manner.

The invention claimed is:

1. A tubular shaft for a tubular shaft instrument comprising:
   a hollow shaft component,
   an actuating rod arranged in the hollow shaft component, and
   functional elements that are attached at a distal end of the hollow shaft component and/or of the actuating rod,
   the actuating rod being axially displaceable relative to the hollow shaft component in order to move distal sections of the functional elements toward one another, past one another, and/or away from one another,
   the actuating rod comprising at least one bending area in which flexible segments and support segments alternate, and in which the actuating rod has significantly less bending resistance than outside the at least one bending area,
   a friction-reducing layer being provided on the at least one bending area of the actuating rod, the friction-reducing layer reducing friction between the actuating rod and an inside wall of the hollow shaft component,
   the flexible segments each comprising a cylindrical section having a smaller cross sectional area than the actuating rod outside the at least one bending area, and
   the support segments each comprising an essentially spherical section with a diameter equal to a diameter of the actuating rod outside the at least one bending area,
   wherein adjacent support segments are interconnected by one of the flexible segments.

2. The tubular shaft for a tubular shaft instrument according to claim 1, wherein the friction-reducing layer has a lower elasticity modulus than the actuating rod.

3. The tubular shaft for a tubular shaft instrument according to claim 1, wherein the friction-reducing layer is formed from shrink tubing.

4. The tubular shaft for a tubular shaft instrument according to claim 1, wherein the actuating rod, with its at least one bending area, is formed as a single piece and/or the actuating rod comprises at least two bending areas.

5. The tubular shaft for a tubular shaft instrument according to claim 1, wherein the at least one bending area comprises a plurality of bending areas formed on the actuating rod, and wherein an area is provided between two adjacent bending areas of the plurality of bending areas where the actuating rod is essentially rigid.

6. The tubular shaft for a tubular shaft instrument according to claim 1, wherein the hollow shaft component has a slotted area on its distal end where a slot spaces or separates two bars from one another, and the functional elements each have at least one passage hole through which an axle extends, said axle being fastened to the bars on both sides of the functional elements.

7. The tubular shaft for a tubular shaft instrument according to claim 1, wherein the functional elements are connected with the actuating rod via a sliding component, and at least one of the functional elements has at least one cam that detachably protrudes into the at least one guide track, which is provided in the sliding component, wherein the cam further extends perpendicular to an axial direction of the tubular shaft.

8. A tubular shaft instrument having the tubular shaft according to claim 1, manufactured using the steps comprising:
   providing the hollow shaft component,
   providing the actuating rod,
   providing the at least one bending area of the actuating rod with the friction-reducing layer,
   inserting the actuating rod into the hollow shaft component in order to create the tubular shaft, and
   bending the tubular shaft in an area that corresponds to the at least one bending area of the actuating rod.

* * * * *